United States Patent [19]

Haubrich

[11] Patent Number: 5,599,652
[45] Date of Patent: Feb. 4, 1997

[54] PEROXYCARBOXYLIC ESTER INITIATORS DERIVED FROM NITROGEN HETEROCYCLES

[75] Inventor: Jeanne E. Haubrich, Maplewood, Minn.

[73] Assignee: Imation Corp., Woodbury, Minn.

[21] Appl. No.: 621,745

[22] Filed: Mar. 22, 1996

Related U.S. Application Data

[62] Division of Ser. No. 407,617, Mar. 21, 1995, Pat. No. 5,527,921.

[51] Int. Cl.$^6$ .............................. G03F 7/031; C08F 2/48; C08F 4/28
[52] U.S. Cl. .................. 430/281.1; 430/920; 430/288.1; 522/13; 522/9; 522/24
[58] Field of Search ............................ 430/281.1, 920; 522/9, 13, 24

[56] References Cited

U.S. PATENT DOCUMENTS

| | | | |
|---|---|---|---|
| 3,352,791 | 11/1967 | Sheehan et al. | 546/102 |
| 4,063,012 | 12/1977 | MacLeay et al. | 526/219 |
| 4,416,826 | 11/1983 | Neckers | 546/245 |
| 4,777,191 | 10/1988 | Komai et al. | 522/46 |
| 4,831,188 | 5/1989 | Neckers | 522/60 |
| 4,946,960 | 8/1990 | Wade et al. | 522/13 |
| 4,950,581 | 8/1990 | Koike et al. | 430/281.1 |
| 4,985,564 | 1/1991 | Kakumaru et al. | 546/102 |

OTHER PUBLICATIONS

Sheppard's *Encyclopedia of Polymer Sci. and Eng.*, 2nd ed., 1988, pp. 1–21.
Gruber, *Prog. Polym. Sci.*, 17, 953 (1992).
Olah et al., *J. Org. Chem.*, 42, No. 1, p. 32 (1977).
Chemical Abstract No. 99:139722z, Peroxide esters of nicotinic acids. Vilenskaya, M. et ., *Vestn. L'vov Politekh Inst.*, 1983, 171, 27–30.
Bischoff, V. C. et al., *Journal für Praktische Chemie*, 312 (1970).
Neckers, D. C., et al., *Tetrahedron Lett.*, 25, 2931 (1984).
Joule, J. A. et al., *Heterocyclic Chemistry*, 2nd ed. Van Nostrand Reinhold Co., Wokingham, Berkshire, England, 1978, pp. 1–16, 357–358.

*Primary Examiner*—Cynthia Hamilton
*Attorney, Agent, or Firm*—Gary L. Griswold; Walter N. Kirn; Arlene K. Musser

[57] ABSTRACT

Peroxycarboxylic ester photoinitiators derived from aromatic nitrogen containing heterocyclic carboxylic acids are described. The heterocyclic aromatic ring may contain additional nitrogen atoms, be fused with another aromatic ring system, be substituted with an additional peroxycarboxylic ester group and/or be substituted with an electron group having a Hammett sigma value greater than 0.1. The peroxycarboxylic ester photoinitiators have been found to be useful in photopolymerizable compositions and photosensitive elements.

8 Claims, No Drawings

PEROXYCARBOXYLIC ESTER INITIATORS DERIVED FROM NITROGEN HETEROCYCLES

This is a division of application Ser. No. 08/407,617 filed Mar. 21, 1995 U.S. Pat. No. 5,527,921.

FIELD OF THE INVENTION

This invention relates to peroxycarboxylic ester photoinitiators, more particularly to peroxycarboxylic ester photoinitiators derived from nitrogen containing aromatic heterocyclic carboxylic acids.

The present invention also relates to a photopolymerizable composition using nitrogen containing aromatic heterocyclic peroxycarboxylic ester photoinitiators and a method for making the photopolymerizable composition. In addition, the present invention relates to the use of the heterocyclic peroxycarboxylic ester photoinitiators in a photosensitive element.

DISCUSSION OF THE PRIOR ART

Organic peroxides have been used extensively as thermal initiators for polymerization. Dialkyl peroxides, diacylperoxides and organic hydroperoxides have been particularly useful as thermal initiators for polymerizations carried out at temperatures below 150° C. For example the following references list examples and uses of peroxides as initiators for polymerizations: Sheppard's *Encyclopedia of Polymer Sci. and Eng.*, 2nd ed., 1988.; Gruber, *Prog. Polym. Sci.*, 17, 953 (1992); and *Organic Peroxides*, Vol. 1, John Wiley & Sons, 1970.

Organic peroxides have not been extensively used as photoinitiators. Photoinitiated polymerizations provide the advantage of carrying out the polymerizations at even lower temperatures than those achieved by typical thermal radical induced decomposition of organic peroxides. Because the organic peroxides are excellent thermal initiators, the shelf-life stability of the initiator in a photopolymerizable composition is a concern. In addition, the organic peroxide needs to be capable of either directly or indirectly, through sensitization, provide initiation upon exposure to commonly used irradiation sources. Most commercial irradiation sources useful for photopolymerization reactions provide output in the 254 nm to 1100 nm range.

Heterocyclic peroxycarboxylic esters derived from nicotinic acid are known, such as those described in Olah, G. A., et al *J. Org. Chem.*, 42, No. 1, p 32 (1977) and Vilenskaya, M., et al *Vestn. L'vov Politekh Inst.* 1983, 171, 27–30. The Olah reference discloses a study of the nucleophilic character of peroxycarboxylic esters in acidic environments. There is no mention of using these types of materials as photoinitiators.

Heterocyclic peroxyesters derived from pyrazole carboxylic acids and isoxazole carboxylic acids are disclosed in Bischoff, V. C., et al., *Journal für Praktische Chemie*, 312 (1970). There is no mention of using these types of materials as photoinitiators. The reference focuses on the use of peroxyester derivatives of acetylene carboxylic acids to synthesize these heterocyclic peroxycarboxylic esters.

Attempts have been made to design a peroxide initiator that is thermally stable and also capable of being directly initiated with light radiation. These initiators are typically derived from known photoactive materials such as benzophenone (for example, European Patent Application No. 0126541 B1 and U.S. Pat. No. 4,950,581 describe the use of polyperoxycarboxylic esters derivatives of benzophenone) or dyes (for example, U.S. Pat. No. 4,063,012 describes the use of peroxycarboxylic ester derivatives of dyes containing heterocyclic structures such as xanthone, thioxanthone, indole, and similar ring systems). Peroxycarboxylic esters derived from acid derivatives of benzothiophene have also been disclosed in Neckers, D. C., et al, *Tetrahedron Lett.*, 25, 2931 (1984). The heterocyclic substituents in the aforementioned peroxy derivatives are electron donating.

To indirectly initiate organic peroxides, the organic peroxide needs to be capable of accepting energy or electron transfer from a photosensitizer. The use of indirect sensitization of an initiator provides more flexibility in matching the sensitivity of the photopolymerization composition to the light source used in the photoinitiation process. Photosensitizers are also generally much more efficient at absorbing light radiation than most initiators. Increased sensitivity of the photopolymerization composition allows one to use relatively lower power light sources. This is a particular advantage in photoresist, printing plates, stereolithography, graphic art films, proofing films and solder mask applications where the trend in the imaging process is moving away from high output kilowatt UV lamps to relatively low output milliwatt laser diodes. Therefore, there is a need for more efficient photoinitiators systems that are compatible with lower output light sources.

SUMMARY OF THE INVENTION

The present invention provides a peroxycarboxylic ester having the following general formula:

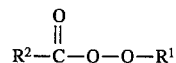

where, $R^1$ is an alkyl group and $R^2$ is a nucleus comprising an aromatic heterocyclic ring containing a first $sp^2$ hybridized nitrogen atom and at least one of the following components; i) an additional $sp^2$ hydridized nitrogen in conjugation with the first $sp^2$ hybridized nitrogen, ii) an aromatic structure fused to the aromatic heterocyclic ring containing the first $sp^2$ hybridized nitrogen, iii) a peroxycarboxylic ester substituent, or iv) an electron withdrawing substituent having a Hammett sigma value greater than 0.1.

In another embodiment, the present invention provides photopolymerizable composition comprising (a) a radically polymerizable compound and (b) a peroxycarboxylic ester photoinitiator having the formula:

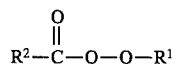

where, $R^1$ and $R^2$ are as defined above.

In another embodiment, the present invention provides a photosensitive imaging element comprising a support having coated thereon at least one photopolymerizable layer comprising; (a) a radically polymerizable compound; (b) a photosensitizer; and (c) a peroxycarboxylic ester photoinitiator having the formula:

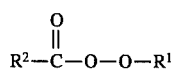

where, $R^1$ and $R^2$ are as defined above.

In still another embodiment, the present invention provides a method of photopolymerization comprising the steps of:

(1) providing a polymerizable composition by combining
  (a) a peroxycarboxylic ester photoinitiator having the formula:

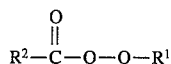

where, $R^1$ and $R^2$ are as defined above;
  (b) a radically polymerizable compound; and
  (c) a photosensitizer to form the polymerizable composition; and
(2) irradiating the polymerizable composition with sufficient electromagnetic radiation to cause polymerization of the polymerizable composition.

Other aspects, benefits and advantages of the present invention are apparent from the following detailed description, examples and claims.

DETAILED DESCRIPTION

The present invention provides a peroxycarboxylic ester having the following general formula;

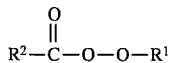

where $R^1$ is an alkyl group, preferably a tertiary alkyl radical. $R^2$ is a nucleus comprising an aromatic heterocyclic ring containing an $sp^2$ hybridized nitrogen atom and at least one of the following components:
  (i) an additional $sp^2$ hybridized nitrogen in conjugation with the first $sp^2$ hybridized nitrogen,
  (ii) an aromatic structure fused to the aromatic heterocyclic ring containing the first $sp^2$ hybridized nitrogen atom,
  (iii) a peroxycarboxylic ester substituent, and
  (iv) an electron withdrawing substituent having a Hammett sigma value greater than 0.1. Preferably, the Hammett sigma value is greater than 0.4.

"Hammett sigma value" is equivalent to the Hammett $\sigma_p$ constant as defined by the Hammett equation $$\log K/K° = \sigma_p \rho$$

where, $K°$ is the acid dissociation constant of the reference in aqueous solution at 25° C., K is the corresponding constant for the para-substituted acid, and $\rho$ is the reaction parameter in which $\rho$ is defined as 1.0 for the dissociation of para-substituted benzoic acids.

"$sp^2$ hybridized nitrogen" as used in the present invention is defined as a nitrogen having three valence bonds comprising a single and double bond (i.e., =N—), all of which are part of a heterocyclic aromatic ring system.

Within the field of organic chemistry and particularly within the field of organic photoinitiators, it is widely understood that significant substitution of compounds is tolerated or even useful. In the practice of the present invention, for example, the term 'alkyl group' allows for substitution on a chemical moiety which is a classic alkyl, such as methyl, ethyl, propyl, hexyl, isooctyl, dodecyl, stearyl, etc. The term 'group' specifically envisions and allows for substitutions on alkyls which are common in the art, such as hydroxy, halogen, nitro, cyano, sulfonate, etc., as well as including an unsubstituted alkyl moiety. Where only an unsubstituted moiety is used, the terms "alkyl" or "alkyl radical" will be used.

The heterocyclic component may contain a five or six membered aromatic ring and may be a single or fused ring system. Examples of suitable nitrogen heteroaromatic compounds include, non-exclusively, the azines, azoles with two or more heteroatoms, and azaazulenes. Examples of suitable azines non-exclusively include; pyridine, pyrazine, pyrimidine, pyridazine, purine, triazines, quinoline, isoquinoline, quinoxaline, quinazoline, phthalazine, cinnoline, pteridine, 4aH-carbazole, acridine, phenanthridine, benzocinnoline, phenanthrolines, and phenazine. Examples of azoles non-exclusively include; imidazole, oxazole, furazan, thiazole, thiadiazoles, oxadiazoles, triazoles, tetrazoles, benzotriazole, benzothiadiazole, benzooxidiazole, 1,2,4-triazolo(1,5-α)pyrimidine, and s-triazolo(4,3,-α)quinoline. Further examples include the combination of one or more of these structures in a larger aromatic compound, such as benzo[h]isoquinoline, 7H-pyrazino[2,3-c]carbazole, furo[3,4-c]cinnoline, 4H-pyrido[2,3-c]carbazole, 5H-pyrido[2,3-d][1,2]oxazine, 1H-pyrazolo[4,3-d]oxazole, 4H-imidazo[4,5-d]thiazole, pyrazino[2,3-d]pyridazine, imidazo[1,2-b][1,2,4]triazine, pyrido[1',2':1,2]imidazo-[4,5-b]quinoxaline, 2,7,9-triazaphenanthrene, and selenazolo[5,4-f]benzothiazole.

The preferred heterocyclic peroxycarboxylic esters for use as initiators that can be photosensitized include peroxycarboxylic esters with two or more $sp^2$ bonded nitrogen atoms in a heterocyclic ring, and peroxycarboxylic esters with one or more aromatic rings fused to the aromatic ring containing the peroxycarboxylic ester. The preferred peroxycarboxylic ester initiators for use without a sensitizer include those having a molar extinction coefficient >1000 at the wavelength used for irradiation.

Heterocyclic compounds useful for this application may also contain substituents on the ring system other than the peroxycarboxylic ester group. Substituents having a positive Hammett sigma value are particularly useful. A positive Hammett sigma value indicates that the group is electron withdrawing. Suitable substituents have Hammett sigma values greater than 0.1, and preferably greater than 0.4. Non-exclusive examples of substituents with this characteristic include cyano, halogeno, formyl, alkoxycarbonyl, hydroxycarbonyl, nitro, acetyl, perfluoroalkyl, and alkylsulfonyl radicals, as well as other groups described in Lange's *Handbook of Chemistry*, 14th edition, McGraw-Hill, Chapter 9, pp 2–7 (1992).

The heterocyclic peroxycarboxylic esters can be easily synthesized from the carboxylic acid derivatives of the heterocyclic compounds. The carboxylic acid may be first converted to the acid chloride using well known methods. In this case the desired alkyl hydroperoxide is added to the heterocyclic carboxy acid chloride to form the corresponding peroxycarboxylic ester.

Commercially available peroxycarboxylic esters such as t-butyl peroxybenzoate often work poorly as sensitized initiators. A possible reason for this is that these initiators are not easily activated by either energy or electron transfer from a sensitizer. One way to improve the sensitization is to make the peroxycarboxylic ester a better electron acceptor. Replacing carbon in an aromatic compound with an $sp^2$ hybridized nitrogen is known to give relatively electron deficient compounds. For example, Wiberg, et. al. *J. Am. Chem. Soc.* 92, 7154 (1969) have shown that, whereas benzene cannot be reduced by standard polarographic potentials, pyridine and other azines are reducible using standard polarographic potentials. Peroxycarboxylic esters derived from the carboxylic acids of aza aromatic compounds, such as the azines and previously mentioned azoles, should be better electron acceptors than the carbocyclic analogs, and therefore better initiators for use with electron donating sensitizers.

The mechanism of sensitization for the heterocyclic peroxycarboxylic esters has not been proven to be electron transfer, but even if other factors play a role, it is still shown that the initiators can give better sensitivity than carbocyclic analogs.

The heterocyclic peroxycarboxylic ester initiators may be used to radically induce photopolymerization either by direct irradiation or by photosensitization. The amount of initiator used will vary depending on the materials to be polymerized, type of source, and other additives, but initiator amounts from 0.05 to 50% of the coating weight, preferably 2–20% and more preferably 3–10% may be used. Since the heterocyclic peroxycarboxylic esters are better electron acceptors than their corresponding carbocyclic compounds, they are particularly useful as initiators in photopolymerizable compositions that are sensitized by a dye which is oxidized upon photoexcitation. The sensitizer is chosen based on the output of the light source used to initiate the polymerization reaction. To be effective the sensitizer must absorb a sufficient amount of radiation to achieve the level of excitation needed to provide sensitization. More than one sensitizer may be used in combination to increase speed or broaden the light response for a particular source. Upon photoexcitation, the sensitizer activates the initiator, causing it to break apart and form radicals that cause polymerization. Examples of suitable sensitizers non-exclusively include, ketone ultraviolet sensitizers, coumarin dyes, xanthene dyes, acridine dyes, thiazole dyes, thiazine dyes, oxazine dyes, azine dyes, cyanine dyes, aminoketones, porphyrins, thioxanthones, aromatic polycyclic hydrocarbons, pyrillium dyes, aminotriaryl methanes, pyridinium dyes, merocyanine dyes, p-substituted aminostyryl ketone compounds, and squarylium dyes. Aminoaryl-ketone and aminocoumarin dyes are the preferred sensitizers for applications requiring high sensitivity (e.g., graphic arts). For applications requiring deep cure (e.g., cure of highly-filled composites), it is preferred to employ sensitizers having an extinction coefficient below about 1000, more preferably below about 100, at the desired wavelength of irradiation for photopolymerization.

Although the concentration ratio of sensitizer to peroxycarboxylic ester initiator will depend upon such factors as the desired use, the selection of sensitizer, etc., generally the molar concentration ratio is between 1/100 to 2/1, respectively, preferably 1/20 to 1/1.

The use of indirect initiation using photosensitizers have been found to be particularly useful in photocuring of solventless coatings and printing inks, and in imaging applications. The heterocyclic peroxycarboxylic ester initiators of the present invention have been shown to increase the efficiency of initiation in photosensitive elements sensitized by dyes that absorb visible light. The greater sensitivity provides the flexibility of using relatively low power lasers as a light source. This is particularly useful for imaging photosensitive elements directly from digital data which eliminates the need for the production of a masking film.

Photopolymerizable compositions typically comprise a radically polymerizable compound and an initiator system. The type of initiator system will vary depending upon the type of polymerizable compound selected and the light source used to initiate the polymerization reaction. Polymerizable compounds having at least one ethylenically unsaturated group are selected based on the characteristics desired in the final radiation cured material. Types of polymerizable compounds include monomers, prepolymers and oligomers, as well as mixtures and copolymers thereof.

Examples of monomers include alkyl esters of unsaturated carboxylic acids and alkyl amides of unsaturated acids. Examples of oligomers and prepolymers having ethylenically unsaturated groups include esters of aliphatic polyols with unsaturated carboxylic acids, amides of aliphatic amines with unsaturated carboxylic acids, acrylated epoxyoligomers, acrylated aliphatic urethane oligomers, acrylated aromatic urethane oligomers, acrylated polyester oligomers, and acrylated acrylic oligomers. Many of these types of materials are commercially available. Other useful examples include the acrylated urethane oligomers described in U.S. Pat. No. 4,304,923; the methacrylated and acrylated sulfocompound oligomers described in U.S. Pat. No. 4,855,384; and the methacrylated and acrylated azlactone derivatives described in U.S. Pat. No. 5,235,015.

The polymerizable composition can optionally contain other materials such as binders, solvents, plasticizers, chain transfer agents, surfactants, stabilizers, indicators, inhibitors, electron donating compounds (such as those listed in European Patent Application 0290133), antistats, and other known fillers or film modifiers. The composition may also contain colorants such as pigments and dyes. Any dye that is soluble in the composition and does not significantly decrease the light sensitivity of the photopolymerizable material, inhibit the polymerization reaction, or migrate excessively to the surface, is suitable. Pigments can be selected from the many types that are commercially available for matching color specifications. The pigment or combinations of pigments can be dispersed by milling the pigment in the photopolymerizable composition. More preferably, the pigment is dispersed by milling the pigment in a dispersing resin or combination of resins and then added to the photopolymerizable composition. The particular type of dispersion resin and the pigment-to-resin ratio chosen will depend on the particular pigment, surface treatment of the pigment, dispersing solvent, milling process, and the quality of dispersion required.

A photopolymerizable composition is formulated by combining the heterocyclic peroxycarboxylic ester initiator with the desired radically polymerizable material. Depending on the light source and sensitivity of the composition, a photosensitizer may optionally be added to enhance the sensitivity. The mixture is then irradiated with the appropriate light source to initiate the polymerization. The light source may be any source of irradiation which is absorbed by the photoinitiator or sensitizer causing radical induced polymerization.

One useful application of these photopolymerizable compositions is in photosensitive imaging elements. An example of a particularly useful photosensitive imaging element comprises a support upon which is coated at least one layer of the photopolymerizable composition. Suitable supports include resin coated paper, various transparent or opaque plastic sheets or films (e.g., polyethylene terephthalate, PET), metal sheets and foils (preferably aluminum substrates that have been grained and anodized).

Due to the oxygen sensitivity of some of the photopolymerizable compositions, it may be necessary to apply an oxygen barrier layer over the top surface of the photopolymerizable layer. Typically the oxygen barrier layer is coated onto the photopolymerizable layer from an aqueous solution. Preferred water soluble resins non-exclusively include alkyl ethers of cellulose, polyvinyl alcohols and polyvinyl pyrrolidone.

The photosensitive imaging element is imaged by irradiation through a reproduction mask or directly by a laser. The image is then developed using a developer solution capable of removing the unwanted non-cured photopolymerizable composition and leaving the cured photopolymerizable composition as a representation of the image. Suitable developer solutions include various combinations of carbonate salts, bicarbonate salts, phosphate salts, surfactants in water or a solvent or solvent mixture.

The invention will now be illustrated in the following non-limiting examples:

EXAMPLES

The following examples illustrate the utility of the peroxycarboxylic ester initiators in a photosensitive element comprising a support, a photopolymerizable layer and a barrier layer. Unless designated otherwise, all materials are available from Aldrich Chemicals, Milwaukee, Wis.

The following photosensitizers were used in the examples:

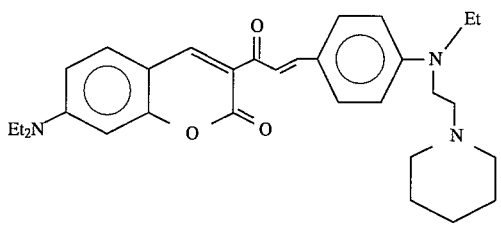

KC-4

Dye [KC-4] was prepared as described in European Patent Application 538997, Example number 3.

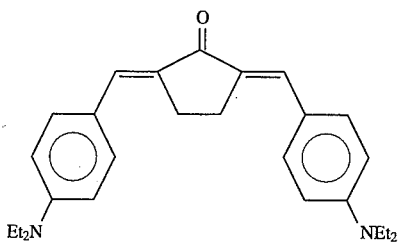

CP1

Dye [CP I] was prepared from cyclohexanone and p-(diethylamino)benzaldehyde by an aldol condensation as taught in Picus, *J. Am. Chem. Soc.*, 70, 3073 (1948).

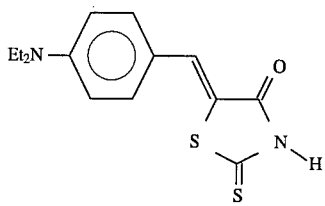

EtAR 5-(4-Diethylaminobenzylidene)rhodanine [EtAR] is available from Aldrich. The following peroxycarboxylic ester initiators were used in the examples.

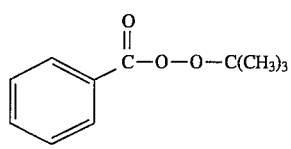

BP t-Butylperoxybenzoate [BP] is available from Aldrich.

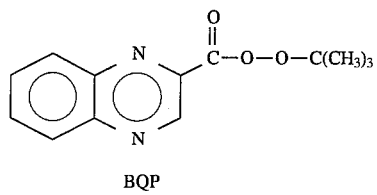

BQP

Synthesis of 2-(t-Butylperoxycarbonyl)quinoxaline [BQP]:

A solution of 0.237 g of 2-Quinoxalyl chloride dissolved in 5 mL of a 1:1 mixture of dichloromethane and benzene was added dropwise to a stirred ice cooled solution of 0.14 g of potassium hydroxide in 0.23 g of t-butylhydroperoxide (90%). The ice bath was removed and the mixture was allowed to stir an additional 1.5 hours at room temperature. The aqueous phase was separated from the organic phase after the addition of more dichloromethane. The organic phase was washed three times with a 10% aqueous sodium hydroxide solution, followed by water and then dried over sodium sulfate. Removal of the solvent gave rise to 0.218 g of a slightly yellow solid. The material was recrystallized from toluene, giving rise to slightly yellow prisms with a melting point of 95°–96° C. Elemental analysis results show 63.4% carbon; 5.6% hydrogen; and 11.2% nitrogen present which is consistent with the formula; $C_{13}H_4N_2O_3$. $^1$H NMR (CDCl$_3$) δ 9.44 (s, 1 H), 8.25 (m, 2 H), 7.9 (m, 2 H), 1.50 (s, 9 H); $^{13}$C NMR(CDCl$_3$) δ 161.9, 144.2, 143.6, 141.4, 141.1, 132.4, 131.0, 130.5, 129.2, 84.8, 26.1; IR (on polymer film) 1757, 1491, 1062 cm$^{-1}$;

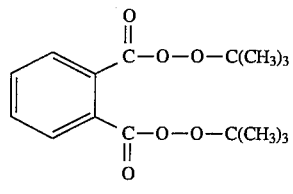

PTP 1,2-Di(t-Butylperoxy)phthalate [PTP] was synthesized from phthaloyl dichloride using a procedure analogous to that described to synthesize BQP.

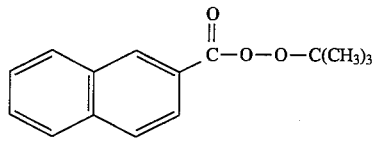

BNP t-Butylperoxynaphthalate [BNP] was synthesized from 2-naphthoyl chloride using a procedure analogous to that described to synthesize BQP.

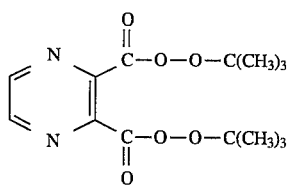

BPP

Synthesis of 2,3-Di(t-butylperoxycarbonyl)pyrazine [BPP]:

To a flask charged with 0.512 g of 2,3-pyrazine dicarboxylic acid was added 3 mL of thionyl chloride and 30 mg of dimethylformamide. The stirred mixture was then heated to reflux under a nitrogen atmosphere. After refluxing for 2.5 hours the solution turned brown. The reaction mixture was allowed to stand for two days at room temperature. After the addition of 10–15 mL of hexane, a brown oil gradually separated from the solution. The hexane was then decanted from the oil; and the oil was placed under vacuum. The oil was picked up in toluene and hexane, then filtered. Removal of the solvent gave rise to 0.45 g of a yellow liquid. $^1$H NMR indicated that at least 90% of the product was the desired acid chloride intermediate.

The acid chloride intermediate was then converted to the diperoxycarboxylic ester using the same general procedure as described in the preparation of BQP described above. Recrystallization from a mixture of ether and hexane gave rise to colorless needles with a melting point of 80°–81° C. Elemental analysis results show 53.5% carbon; 6.4% hydrogen; and 8.9% nitrogen present which is consistent with the formula; $C_{14}H_{20}N_2O_6$. $^1$H NMR (CDCl$_3$) δ 8.83 (s,1 H), 1.46 (s, 9 H); $^{13}$C NMR (CDCl$_3$) δ 162, 146, 143, 85, 26; IR (on polymer film) 1770, 1755, 1109, 1050 cm$^{-1}$;

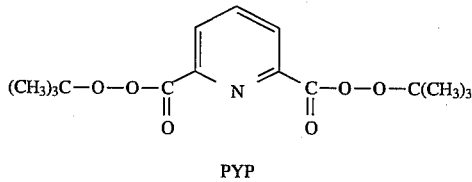

PYP

Synthesis of 2,6-Di-(t-butylperoxycarbonyl)pyridine [PYP]:

The acid chloride of 2,6-pyridinedicarboxylic acid was prepared using the same procedure as described in the preparation of BPP described above. The 2,6-pyridinedicarboxylic acid chloride was then converted to the diperoxycarboxylic ester using the same procedure as described in the preparation of BQP described earlier. Recrystallization from a mixture of toluene and hexane gave rise to colorless needles with a melting point of 107°–108° C. Elemental analysis results show 57.8% carbon; 6.7% hydrogen; and 4.4% nitrogen present which is consistent with the formula; $C_{15}H_{21}NO_6$. $^1$H NMR (CDCl$_3$) δ 8.26 (d, 2 H, J=7.7 Hz), 8.05 (t, 1 H, J=7.7 Hz), 1.46 (s, 9 H); $^{13}$C NMR (CDCl$_3$) δ 162, 147, 138, 128, 84, 26; IR (coated on a polymer film) 1761, 1583, 1170, 1064 cm$^{-1}$;

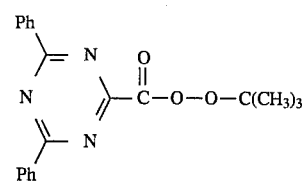

BTP

Synthesis of 2-t-butylperoxycarbonyl-4,6-diphenyl-1,3,5-triazine [BTP]:

2-Methyl-4,6-diphenyl-1,3,5-triazine was prepared using the method described in Gillespie, J. S. Jr., et al, *J. Heterocyclic Chem.*, 8, 723 (1971). The methyl triazine was then oxidized to the potassium carboxylate salt using the method described in Grundman, C., et al, *Chem. Bet.*, 84, 648 (1951). The salt was then converted to the acid and the acid convened to the peroxycarboxylic ester using the same procedure used in the preparation of BQP described earlier. The resulting colorless solid had a melting point of 128°–130° C. Elemental analysis results show 68.4% carbon; 5.6% hydrogen; and 12.0% nitrogen present which is consistent with the formula; $C_{20}H_{19}N_3O_3$. $^1$H NMR (CDCl$_3$) δ 8.67 (dd, 4, J=7.1, 1.5 Hz), 7.6 (m, 6), 1.51 (s, 9); $^{13}$C NMR (CDCl$_3$) δ 172.5, 163.8, 161.0, 134.5, 133.4, 128.1, 128.7, 84.9, 26.1; IR (coated on a polymer film) 1781, 1541, 1515, 1373 cm$^{-1}$;

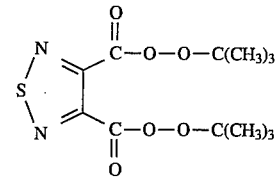

TZP

Synthesis of 3,4-Di(t-butylperoxycarbonyl)-1,2,5-thiadiazole [TZP]:

The preparation described in Warren, J. D., et al, *J. Heterocyclic Chem.* 16, 1817 (1979) was used to prepare 1,2,5-thiadiazole-3,4-dicarboxylic acid from diaminomaleonitrile. At room temperature, 4.30 g of p-toluenesulfonyl chloride was added to a solution of 0.990 g of 1,2,5-thiadiazole-3,4-dicarboxylic acid in 10 mL of pyridine. The solution was cooled in an ice bath and 1.09 g of t-butylhydroperoxide (90% solution in water) was added. The solution was stirred for one hour during which it was cooled with an ice bath such that the temperature was as low as possible without freezing the pyridine. The solution was then poured into a mixture of water and toluene. The toluene layer was separated and washed twice with a 10% aqueous sodium hydroxide solution. The toluene solution was then dried over sodium sulfate and the solvents removed giving rise to 1.414 g of a yellow liquid. The yellow liquid was purified by column chromatography to give a colorless solid with a melting point of 39°–41° C.; $^1$H NMR (CDCl$_3$) δ 1.42 (s); IR (coated on a thin polymer film) 1784, 1132, 1019 cm$^{-1}$;

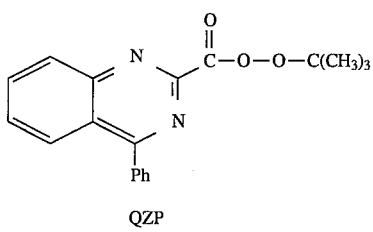

QZP

Synthesis of 2-5-Butylperoxycarbonyl-4-phenylquinazoline [QZP]:

The preparation described in Bergman, J., et al, *Tetrahedron*, 42, 3697 (1986) was used to prepare 2-carboethoxy-4-phenylquinazoline from 2-aminobenzonitrile. The ester was hydrolyzed to the acid, which was convened to QZP using the same procedure used in the preparation of BQP. The resulting colorless crystals had a melting point of 147°–149° C.; $^1$H NMR (CDCl$_3$) δ 8.31 (d, 1), 1.23 (d, 1), 8.00 (m, 1), 7.85 (m, 2), 7.75 (m, 1), 7.60 (m, 3), 1.48 (s, 9); IR (coated on a thin polymer film) 1773, 1097 cm$^{-1}$.

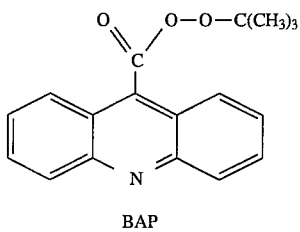

BAP

Synthesis of 9-t-Butylperoxycarbonylacridine [BAP]:

Acridine-9-carboxylic acid monohydrate was converted to the peroxycarboxylic ester using the same general procedure used in the preparation of TZP. The crude product was purified by column chromatography to give a 28% yield of a light yellow powder having a melting point of 132°–134° C.; $^1$H NMR (CDCl$_3$) δ 8.29 (d, 2, J=8 Hz), 8.08 (d, 2, J=8 Hz), 7.84 (m, 2), 6.50 (m, 2), 1.46 (s, 9); IR (coated on a thin polymer film) 1764, 1181, 756 cm$^{-1}$.

EXAMPLES 1–19

Examples 1–19 illustrate the use of the peroxycarboxylic ester initiators in a photosensitive element. The following photopolymerizable coating solution using the photosensitizer and peroxycarboxylic ester initiator designated in Table 1 was used in the preparation of Examples 1–19:

| | |
|---|---|
| Methacrylate photopolymerizable polymer[1](33% in MEK) | 1.0 g |
| Pentaerythritol tetraacrylate (SR-295 available from Sartomer Co., Westchester, PA; 50% in Methyl ethyl ketone) | 0.4 g |
| Photosensitizer | 0.015 g |
| Methyl ethyl ketone | 6.0 g |
| Peroxycarboxylic ester initiator | .06–.08 g |

[1]Preparation of the methacrylate photopolymerizable polymer is described in Example 4 of Ali, et al, U.S. Pat. No. 5,235,015. A 95:5 weight % copolymer of VDM (2-vinyl-4,4-dimethyl-2-oxazoline-5-one) and (2-methacryloxyethyl)-1-hexadecyldimethylammonium bromide (DMAEMA-C$_{16}$) was functionalized by reacting with 0.7 equivalents of 2-hydroxyethylmethacrylate (HEMA), 0.1 equivalent of aspartic acid monotetrabutylammonium salt (ASATBA) and 0.2 equivalents of water, all equivalents with respect to VDM.

Each of the photopolymerizable coating solutions for Examples 1–19 listed in Table 1 was coated, in red light, onto a silicated aluminum base using a #10 wire wound bar. The coating was dried using a heat gun for 30 seconds giving rise to an approximate coating weight of 1.4 g/m$^2$. An oxygen barrier layer solution consisting of 5% by weight poly(vinyl alcohol) (V540 available from Air Products and Chemicals, Inc., Allentown, Pa.) and 0.1% by weight Triton X-100 (octylphenoxypolyethoxyethanol nonionic surfactant available from Union Carbide Chemicals and Plastics Co., Inc., Danbury, Conn.) in water was coated over the photopolymerizable layer using a #16 wire wound bar. The barrier layer was dried using a heat gun for one minute giving rise to an approximate coating weight of 2.1 g/m$^2$.

The photopolymerizable elements generated in Examples 1–19 were exposed with a 16,000 foot candle tungsten source through a 488 nm bandpass filter and a 21 step 1.41 neutral density step wedge. Examples 1–4 were exposed for 30 seconds and Examples 5–19 were exposed for 15 seconds. The elements were developed in a Model 1124 Viking™ plate processor (available from 3M) using a plate developer solution comprising 98.7% by weight water, 0.8% by weight sodium bicarbonate, 0.5% by weight Pelex™ NBL (sodium alkylnaphthalenesulfonate surfactant available from KAO, Tokyo, Japan). Sensitivities were determined by observing the number of imaged solid steps visible on the plate after processing. Table 1 summarizes the sensitivities of coatings made using peroxycarboxylic ester initiators sensitized to 488 nm using different sensitizing dyes.

TABLE 1

| Example No. | Photosensitizer | Initiator | Relative Sensitivity (No. of Solid Steps) |
|---|---|---|---|
| 1 | EtAR | BQP | 5 |
| 2 comparative | EtAR | BNP | 0 |
| 3 | EtAR | BPP | 4 |
| 4 comparative | EtAR | PTP | 0 |
| 5 | CP1 | BQP | 7 |
| 6 comparative | CP1 | BNP | 1 |
| 7 | CP1 | BPP | 7 |
| 8 comparative | CP1 | PTP | 2 |
| 9 | CP1 | PYP | 4 |
| 10 | KC-4 | BQP | 11 |
| 11 comparative | KC-4 | BNP | 7 |
| 12 | KC-4 | BPP | 10 |
| 13 comparative | KC-4 | BP | 6 |
| 14 comparative | KC-4 | PTP | 8 |
| 15 | KC-4 | PYP | 8 |
| 16 | KC-4 | TZP | 9 |
| 17 | KC-4 | QZP | 9 |
| 18 | KC-4 | BTP | 10 |
| 19 | KC-4 | BAP | 10 |

Table 1 shows that heterocyclic peroxycarboxylic ester initiators in formulations sensitized by a dye gave significantly better sensitivities than the carbocyclic peroxycarboxylic ester analogs in the comparative Examples 2, 4, 6, 8, 11, 13 and 14. The degree of increase in sensitivity depends both upon the heterocyclic initiator and the dye used. As much as an eight fold increase in sensitivity was observed.

EXAMPLE 20

The following photopolymerizable coating solution was prepared:

| | |
|---|---|
| Methacrylate photopolymerizable polymer[1] (33% in MEK) | 2.4 g |
| Pentaerythritol tetraacrylate, (SR-295 available from Sartomer Co., Westchester, PA); 50% in methyl ethyl ketone) | 1.2 g |
| Pigment Disperson[2] (34% in methyl ethyl ketone) | 0.6 g |
| Methyl ethyl ketone | 18.0 g |
| BQP | .06–.08 g |

[1] Preparation of the methacrylate photopolymerizable polymer is described in Example 4 of Ali, et al, U.S. Pat. No. 5,235,015.
[2] The Pigment dispersion consisted of 13.6% by weight cyan pigment, 13.6% by weight RJ-100, 2.2% by weight vinyl chloride/vinyl acetate/vinyl alcohol, 0.7% by weight Disperby K (available from RBH dispersions, Bound Brook, NJ)

The coating solution was coated on to silicated aluminum base using a #10 wire wound bar in a red light environment. The coating was dried using a heat gun for 30 seconds giving rise to an approximate coating weight of 1.4 g/m$^2$. An oxygen barrier layer solution consisting of 5% by weight poly(vinyl alcohol) (V 540 available from Air Products and Chemicals Inc., Allentown, Pa.) and 0.1% by weight Triton X-100 (octylphenoxypolyethoxyethanol nonionic surfactant available from Union Carbide Chemicals and Plastics Co., Inc., Danbury, Conn.) in water was coated over the photopolymerizable layer using a #16 wire wound bar. The barrier layer was dried using a heat gun for one minute giving rise to an approximate coating weight of 2.1 g/m$^2$.

The photosensitive element was irradiated through a 21 step 1.41 neutral density step wedge with a 2 KW Berkey Ascor exposure source equipped with a photopolymer lamp for approximately 11 seconds. The element was then developed in a Model 1124 Viking™ plate processor (available from 3M) using a plate developer solution comprising 98.7% by weight water, 0.8% by weight sodium bicarbonate, 0.5% by weight Pelex™ NBL (sodium alkylnaphthalenesulfonate surfactant available from KAO, Tokyo, Japan). The imaged photosensitive element held 3 solid imaged steps.

EXAMPLE 21

A photopolymer composition was prepared identical to that used in Example 20 except BAP was used as the initiator instead of BQP. The sample was imaged and developed as in Example 20. The imaged photosensitive element held 12 solid imaged steps.

Reasonable variations and modifications are possible from the foregoing disclosure without departing from either the spirit or scope of the invention as claimed.

What is claimed:

1. A photopolymerizable composition comprising;
   (a) a radically polymerizable compound; and
   (b) a peroxycarboxylic ester photoinitiator having the formula:

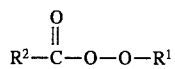

where,
   R$^1$ is an alkyl group; and
   R$^2$ is an aromatic heterocyclic ring containing a first sp$^2$ hybridized nitrogen atom having three valence bonds consisting of a single and double bond forming part of said aromatic heterocyclic ring, and at least one additional component selected from the group consisting of
   i) an additional sp$^2$ hydridized nitrogen having three valence bonds consisting of a single and double bond in conjugation with said first sp$^2$ hybridized nitrogen,
   ii) an alkyl peroxycarboxylic ester substituent, and
   iii) an electron withdrawing substituent having a Hammett sigma value greater than 0.1.

2. The photopolymerizable composition of claim 1 further comprising a photosensitizer.

3. The photopolymerizable composition of claim 1 wherein said aromatic heterocyclic ring is a five membered ring.

4. The photopolymerizable composition of claim 1 wherein said aromatic heterocyclic ring is a six membered ring.

5. The photopolymerizable composition of claim 1 wherein said alkyl group of said peroxycarboxylic ester photoinitiator is a t-butyl radical.

6. The photopolymerizable composition of claim 1 wherein said electron withdrawing substituent has a Hammett sigma value greater than 0.4.

7. A method of photopolymerization comprising the steps of;
   (1) providing a polymerizable composition by combining
      (a) a peroxycarboxylic ester photoinitiator having the formula:

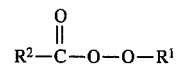

where,
   R$^1$ is an alkyl group; and
   R$^2$ is an aromatic heterocyclic ring containing a first sp$^2$ hybridized nitrogen atom having three valence bonds consisting of a single and double bond forming part of said aromatic heterocyclic ring, and at least one additional component selected from the group consisting of
   i) an additional sp$^2$ hydridized nitrogen having three valence bonds consisting of a single and double bond in conjugation with said first sp$^2$ hybridized nitrogen,
   ii) an alkyl peroxycarboxylic ester substituent, and
   iii) an electron withdrawing substituent having a Hammett sigma value greater than 0.1;
      (b) a radically polymerizable compound; and
      (c) a photosensitizer to form said polymerizable composition and
   (2) irradiating said polymerizable composition with sufficient electromagnetic radiation to cause polymerization of said polymerizable composition.

8. A photopolymerizable composition comprising;
   (a) a radically polymerizable compound; and (b) a peroxycarboxylic ester photoinitiator having the formula:

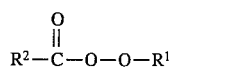

where, $R^1$ is an alkyl group; and $R^2$ is an aromatic heterocyclic ring containing a first $sp^2$ hybridized nitrogen atom having three valence bonds consisting of a single and double bond forming part of said aromatic heterocyclic ring, and at least one aromatic structure fused to said aromatic heterocyclic ring containing said first $sp^2$ hybridized nitrogen atom, wherein said aromatic heterocyclic ring is selected from the group consisting of pyrazine. pyrimidine, pyridazine, triazine, imidazole, furazan, oxazole and thiazole.

* * * * *

UNITED STATES PATENT AND TRADEMARK OFFICE
CERTIFICATE OF CORRECTION

PATENT NO.    : 5,599,652
DATED         : February 4, 1997
INVENTOR(S)   : Jeanne E. Haubrich It is certified that error appears in the above-identified patent and that said Letters Patent is hereby corrected as shown below:

Title page, item [73], Assignee: Imation Corp, Woodbury, Minnesota should read--
Minnesota Mining and Manufacturing Company, St. Paul, Minnesota--.

Signed and Sealed this

Sixteenth Day of December, 1997

Attest:

BRUCE LEHMAN

*Attesting Officer*            *Commissioner of Patents and Trademarks*